United States Patent [19]

Yamane

[11] Patent Number: 5,443,503
[45] Date of Patent: Aug. 22, 1995

[54] ARTIFICIAL HEART PUMP

[75] Inventor: Takashi Yamane, Tsukuba, Japan

[73] Assignees: Agency of Industrial Science & Technology; Ministry of International Trade & Industry, both of Tokyo, Japan

[21] Appl. No.: 194,459

[22] Filed: Feb. 8, 1994

[30] Foreign Application Priority Data

Feb. 18, 1993 [JP] Japan .................. 5-053081

[51] Int. Cl.[6] .............................................. A61M 1/12
[52] U.S. Cl. ............................ 623/3; 417/371; 600/16
[58] Field of Search ................. 623/3; 600/16, 17; 417/371; 415/900

[56] References Cited

U.S. PATENT DOCUMENTS

| | | | |
|---|---|---|---|
| 797,059 | 8/1905 | Hedlund | 417/371 |
| 4,173,796 | 11/1979 | Jarvik . | |
| 4,763,032 | 8/1988 | Bramm et al. | 623/3 X |
| 4,779,614 | 10/1988 | Moise | 600/16 |
| 4,944,748 | 7/1990 | Bramm et al. . | |
| 4,984,972 | 1/1991 | Clausen et al. . | |
| 4,994,078 | 2/1991 | Jarvik | 623/3 |
| 5,154,587 | 10/1992 | Mori et al. | 417/420 |
| 5,205,721 | 4/1993 | Isaacson | 417/356 |
| 5,344,443 | 9/1994 | Palma et al. | 623/3 |

OTHER PUBLICATIONS

Proceedings of the Annual International Conference of the IEEE Engineering in Medicine and Biology Science, vol. 13, No. 5, 1991, pp. 2127–2128, I. Sakuma, et al., "Development of a Novel Direct Motor Driven Seal-less Centrifugal Blood Pump (Baylor Gyro Pump)".

Primary Examiner—David H. Willse
Attorney, Agent, or Firm—Oblon, Spivak, McClelland, Maier & Neustadt

[57] ABSTRACT

An artificial heart pump comprises a cylindrical stator provided between the inner surface of a casing and a rotor so as to establish a blood flow channel between the outer surface of the stator and the inner surface of the casing, and a rotating magnet and a stationary magnet differing in length in their N-S pole directions provided on the rotor and the stator with their N-S pole directions aligned parallel with the axis of rotation, the boundary between the N and S poles of the rotating magnet being positioned closer to a pivot than the boundary between the N and S poles of the stationary magnet.

5 Claims, 2 Drawing Sheets

ARTIFICIAL HEART PUMP

BACKGROUND OF THE INVENTION

1. Field of the Invention

This invention relates to a centrifugal artificial heart pump for surgical implantation in a human patient, more specifically to a centrifugal artificial heart pump whose rotor is suspended in a noncontacting state by magnetic force.

2. Description of the Prior Art

Artificial heart pumps can be classified into the reciprocating type, the rotary displacement type, and the turbo type that operates by rotational flow. Typical of the turbo type that operates by rotational flow is the centrifugal type.

Artificial heart pumps of the centrifugal type are generally equipped with a casing, a rotor disposed inside the casing, a motor for rotating the rotor, a blood flow channel for introducing and guiding the flow of blood, and an impeller that rotates integrally with the rotor for imparting centrifugal force to the blood flowing in through the blood flow channel formed in the casing.

The prior art centrifugal type artificial heart uses ball bearings for rotatably supporting the rotor provided with the impeller. With this system, however, blood flow is liable to stagnate in the vicinity of the ball bearing. Since the formation of stagnant blood is known to be a primary cause of blood coagulation (thrombogenesis), an artificial heart pump that is susceptible to such stagnation has a major defect.

For eliminating this drawback, there have been proposed pumps whose rotors are suspended in a noncontacting state by magnetic force.

U.S. Pat. No. 4,688,998, for example, teaches a pump whose rotor is suspended by electromagnets. The pump's magnetic suspension system constantly maintains the rotor in the proper attitude by regulating the current supplied to the electromagnets so as to control their magnetic force. With this system for supporting the rotor by the force of electromagnets, however, there is a danger that anomalies arising in the control system during pump operation may disturb the attitude of the rotor and, as a result, disrupt the normal flow of blood.

For overcoming this problem, there was proposed a pump of the type shown in FIG. 4 which uses permanent magnets for suspending the rotor. As shown, the pump's rotor 21 is provided with permanent magnets 22 and its casing 26 is provided with permanent magnets 23, with like poles of the two sets of permanent magnets facing each other so as to magnetically suspend the rotor 21. In addition, a pivot 25 is formed on the rear surface of an impeller 24 provided at one end of the rotor 21. The rotor 21 and the impeller 24 are thus mechanically supported on the casing 26 at a single point by the pivot 25.

In the prior art artificial heart pump shown in FIG. 4, the blood flow channel 27 for introducing and guiding the flow of blood consists of a hole passing axially through the center of the rotor 21 so as to enable the blood to be passed to near the center of the impeller 24.

It goes without saying that it is inadmissible for an artificial heart pump to promote blood coagulation (thrombogenesis) or blood cell destruction (hemolysis).

Coagulation (thrombogenesis) is likely to occur where there is blood flow stagnation, while blood cell destruction (hemolysis) is apt to occur when blood enters narrow gaps where rotation and sliding arises or at places where a sharp change in the direction of blood flow occurs.

Since the blood flow channel 27 of the prior art artificial heart pump shown in FIG. 4 is provided inside the rotor 21, it is not possible to achieve a sufficient amount of blood flow. Any attempt to increase the amount of blood flow requires an increase in the diameter of the rotor 21 and thus enlarges the size of the artificial heart pump.

Enlarging the diameter of the rotor 21 for increasing the amount of blood flow also leads to a proportional increase in the circumferential velocity of outer surface of the rotor 21. Since this in turn increases the shear force acting on blood entering the suspension gap 28, it promotes hemolysis.

Although this cause for hemolysis can be alleviated by increasing the size of the suspension gap 28, doing this has the effect of increasing the likelihood of thrombogenesis by making it easier for blood to stagnate or flow backward in the suspension gap 28. It is also apt to reduce the pump output.

Since increasing the suspension gap 28 also reduces the magnetic repulsion that maintains it, it makes it difficult to maintain the proper attitude of the rotor 21.

Further, since as shown in FIG. 4 the rotating permanent magnets 22 and the stationary permanent magnets 23 are oriented radially, the magnetic repulsion between them is unstable. This also makes it difficult to maintain the rotor 21 in the proper attitude.

Owing to this radial orientation, moreover, the rotating permanent magnets 22 and the stationary permanent magnets 23 do not impart a force to the rotor 21 in its axial direction. Since this means that no force is produced for holding the pivot 25 in contact with the casing 26, the attitude of the rotor 21 is unstable.

In addition, owing to the configuration of the blood flow channel 27 inside the rotor 21, the blood is forced to flow turbulently through a narrow flow passage. This increases the risk of hemolysis, as does the fact that direction of blood flow is deflected perpendicularly at the time it collides with the impeller 24.

One object of this invention is to provide a pump for a centrifugal type artificial heart which enables securement of a sufficiently large blood flow amount and which does not readily cause blood coagulation or blood cell destruction.

Another object of the invention is to provide a pump for a centrifugal type artificial heart which enables the rotor thereof to be constantly maintained in the proper attitude.

SUMMARY OF THE INVENTION

For achieving the aforesaid object, this invention provides an artificial heart pump comprising a cylindrical casing closed at one end by a floor, a rotor rotatably disposed in the casing, a cylindrical stator provided between the casing and the rotor and establishing a blood flow channel between its outer surface and the inner surface of the casing, an impeller provided to rotate integrally with the rotor for imparting centrifugal force to blood flowing through the blood flow channel, stationary magnetic means constituted as at least one permanent magnetic provided on the inner surface of the stator, rotating magnetic means constituted as at least one permanent magnet provided on the rotor for producing between itself and the stationary magnetic means a force of magnetic repulsion for supporting the rotor in a noncontacting state with respect to the stator, and a pivot provided at the rotational center of the rear surface of the impeller to abut on the floor of the casing.

Thus in the artificial heart pump according to the present invention a cylindrical stator is disposed between the inner surface of the casing and the rotor so as to form a blood flow channel between the outer surface of the stator and the inner surface of the casing. Therefore, by establishing a large gap between the inner surface of the casing and the outer surface of the cylindrical stator it becomes possible to enlarge the sectional area of the blood flow channel and thus to increase the amount of blood flow, without greatly increasing the overall size of the device. Moreover, since neither of the members constituting the flow channel moves, there is no danger of blood cell destruction owing to rotation.

In addition, the rotor can be made to press constantly onto the floor of the casing by using N-S pole magnets as the magnetic means provided on the stator and the rotor and positioning the boundary line between the N and S poles of the rotating magnets on the pivot side of the boundary line between the N and S poles of the stationary magnets. The pressure produced in this way prevents the rotor from being ejected from the casing as might otherwise happen should an imbalance arise between the magnets.

The above and other features of the present invention will become apparent from the following description made with reference to the drawings.

DESCRIPTION OF THE PREFERRED EMBODIMENT

Figure 1:
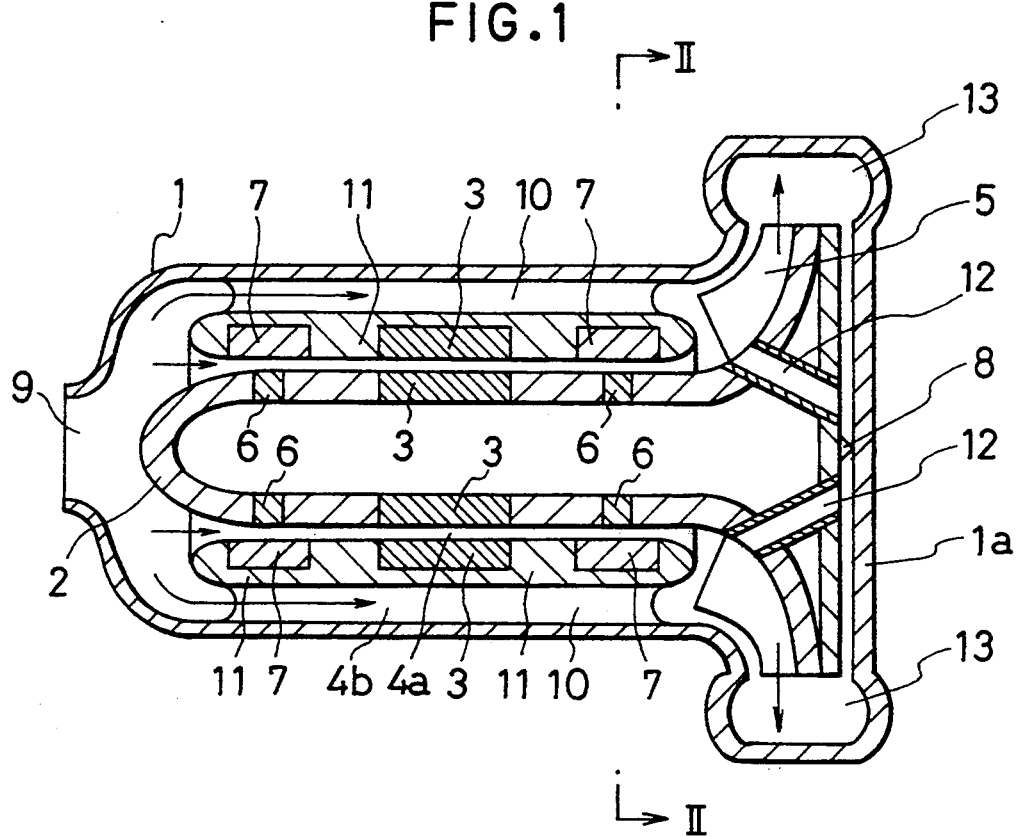
FIG. 1 is a longitudinal sectional view of a centrifugal type artificial heart pump that is an embodiment of the present invention.
Figure 2:
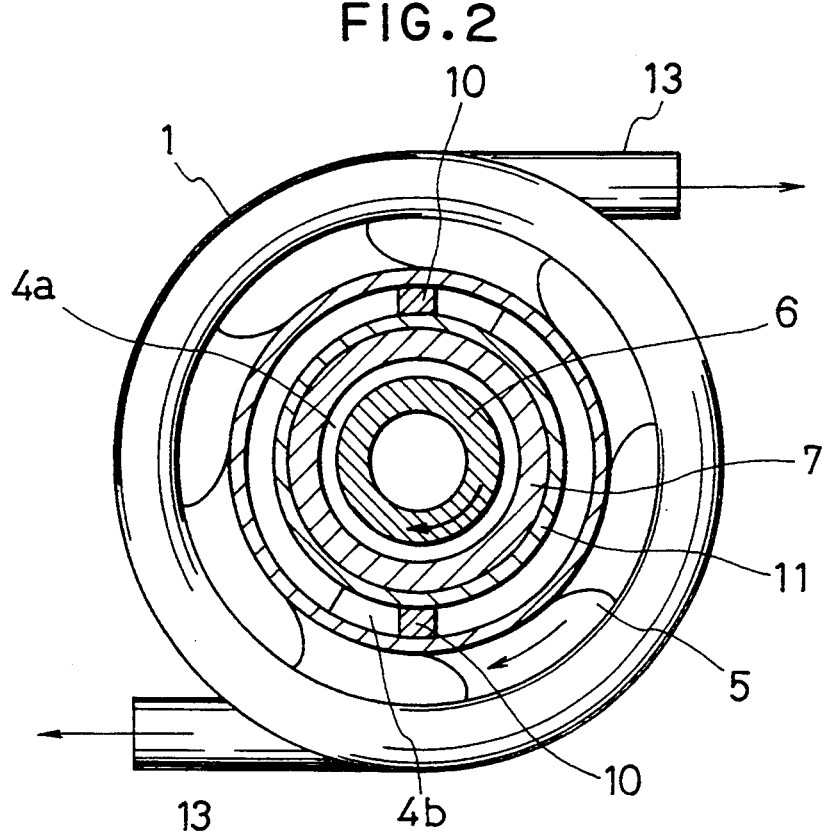
FIG. 2 is a cross-sectional view taken along line II—II in FIG. 1.

An embodiment of the present invention will be explained with reference to FIGS. 1 and 2. The artificial heart pump comprises a casing 1, a rotor 2 disposed inside the casing 1, a motor 3 for rotating the rotor 2, a blood flow channel 4b for introducing and guiding the blood flow, a magnetic suspension gap 4a, an impeller 5 provided inside the casing 1 to rotate integrally with the rotor 2 for imparting centrifugal force to blood flowing through the blood flow channel 4b, rotating permanent magnets 6 provided on the rotor 2, stationary permanent magnets 7 provided at positions opposed to the outer surfaces of the rotating magnets 6 for producing between themselves and the rotating magnets 6 magnetic repulsion for supporting the rotor 2 in a noncontacting state, and a pivot 8 provided at the rotational center of the rear surface of the impeller 5 for supporting the impeller 5 by abutment on the inner surface of the casing 1.

One end of the cylindrical casing is formed with a blood inlet 9 and the other end is closed by a floor 1a. A stator 11 is supported on the inner surface of the casing 1 by a pair of stays 10, 10. The stator 11 is formed approximately cylindrical in section. The rotor 2 is closed at its forward end by a hemispherical portion and is formed approximately cylindrical in section. The casing 1, the stator 11 and the rotor 2 are disposed coaxially.

The stator 11 and the rotor 2 are provided with a DC brushless motor, an AC induction motor or other such brushless motor (referred to simply as a motor herein). The motor 3 rotates the rotor 2. (If a DC brushless motor is used, a rotating speed detector or other such automatic control system (not shown) is provided for controlling the rotational speed of the rotor 2 to a prescribed value.)

Figure 3:
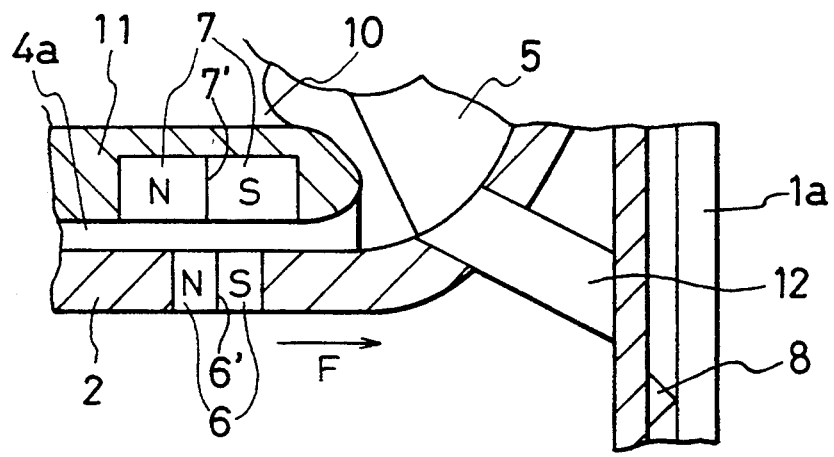
FIG. 3 is an enlarged view of a part of the artificial heart pump of FIG. 1 showing an example of the positioning of the stator and rotor magnets.
Figure 4:
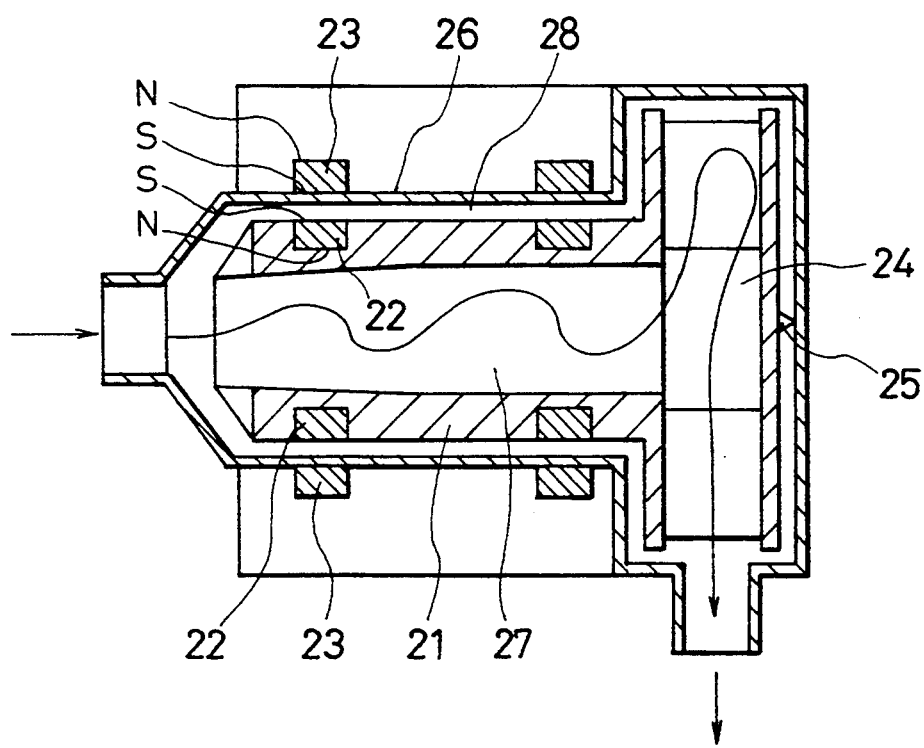
FIG. 4 is a longitudinal sectional view of an example of a prior art centrifugal type artificial heart pump.

Two rotating magnets 6 are provided on the rotor 2, one on either side of the motor 3, and two stationary magnets 7 are similarly provided on the stator 11. This arrangement optimizes stability. The rotating magnets 6 and the stationary magnets 7 are formed to be annular. Their arrangement will be better understood from FIG. 3 taken in conjunction with FIGS. 1 and 2. Both the rotating magnets 6 and the stationary magnets 7 have their N-S pole directions aligned parallel with the axis of rotation of the rotor 2 (the axial direction) but have different lengths in the axial direction. While the rotating magnets 6 are shorter than the stationary magnets 7 in the illustrated embodiment, the invention is not limited to this arrangement and the relationship can be reversed. In addition, the boundary lines between the N and S poles of the rotating magnets 6 (i.e. the centers of the rotating magnets 6 in the axial direction) are positioned on the pivot 8 side of the boundary lines between the N and S poles of the stationary magnets 7 (i.e. the centers of the rotating magnets 7 in the axial direction).

The rotating magnets 6 and the stationary magnets 7 are arranged in the foregoing manner so as to produce a force in the direction of the offset and this force holds the pivot 8 of the rotor 2 firmly in contact with the floor of the casing 1 and thus ensures that the rotor 2 is reliably supported in the suspended state. More specifically, when the boundaries 6', 7' of a rotating magnet 6 and the stationary magnet 7 associated therewith are aligned with each other, the force between the two magnets are balanced so that no force tending to offset them from each other arises. Once the boundaries become even slightly out of alignment, however, the force balance is upset and a force acting to throw them even further out of alignment is produced.

Owing to the aforesaid arrangement of each rotating magnet 6 and associated stationary magnet 7, the N and S poles of each magnet repel the N and S poles of the other. As a result, magnetic repulsion is produced for supporting the rotor 2 in a suspended state while, at the same time, a force F is produced in the axial direction of the rotor 2 for pressing the pivot 8 onto the floor of the casing 1.

Since the forward end of the rotor 2 is closed, the interior of the rotor 2 does not constitute a part of the blood flow channel. Instead, as shown in the illustrated embodiment, the blood flow channel 4b is established between the outer surface of the stator 11 and the inner surface of the casing 1. Although the magnetic suspension gap 4a between the stator 11 and the rotor 2 passes a small amount of blood, it does not operate essentially as a flow channel for blood.

The impeller 5 is formed with washout holes 12 that communicate its front and back sides. By passing blood exiting from the blood flow channel 4b toward the pivot 8 and also passing blood in the vicinity of the pivot 8 to the front surface of the impeller 5, the washout holes 12 prevent blood from stagnating in the vicinity of the pivot 8. The number of washout holes 12 is not specifically defined and one or more such passages can be provided as required.

The other end of the casing 1 (i.e. the end closed by the floor 1a) is provided with an outlet 13 for delivering to the exterior the blood imparted with centrifugal force by the impeller 5.

The operation of the artificial heart pump configured in the foregoing manner will now be explained.

Magnetic repulsion arises between the N and S poles of the stationary magnets 7 of the stator 11 and the N and S poles of the rotating magnets 6 of the rotor 2. As a result, the rotor 2 is suspended in a noncontacting state with respect to the stator 11.

The motor 3 rotates the suspended rotor 2. The impeller 5 rotates integrally with the rotor 2 and draws in blood through the inlet 9 of the casing 1. The blood drawn in flows through the blood flow channel 4b toward the impeller 5. Since the blood flow channel 4b can be formed to have a large sectional area, a high rate of blood flow can be achieved. Although a blood flow stagnation tends to form in the vicinity of the pivot 8, this tendency is counteracted by the action of the washout holes 12, which pass blood from the front surface of the impeller 5 toward the pivot 8 and also pass blood from the pivot 8 to the front surface of the impeller 5. Moreover, the blood is expelled from the outlet 13 by the centrifugal force imparted thereto by the impeller 5. In addition, although a part of the blood flowing against the rotor 2 enters the magnetic suspension gap 4a, it is prevented from stagnating therein by the low pressure constantly maintained at the downstream end.

Further, since the boundary lines between the N and S poles of the rotating magnets 6 are offset toward the pivot 8 relative to the boundary lines between the N and S poles of the stationary magnets 7, an imbalance arises between the forces acting parallel to the axis of rotation, whereby the force acting on the rotor 2 in the axial direction is increased to a force F working to press the pivot 8 of the rotor 2 onto the floor 1a of the casing 1. As a result, the pivot 8 is able to reliably support the rotor 2.

The present invention has thus been shown and described with reference to a specific embodiment. However, it should be noted that the present invention is in no way limited to the details of the described arrangements but changes and modifications may be made without departing from the scope of the appended claims.

For example, although the foregoing embodiment uses permanent magnets for suspending the rotor, the invention is not limited to this arrangement and it is alternatively possible to use electromagnets together with permanent magnets.

Moreover, while the stationary magnets are longer than the rotating magnets in the foregoing embodiment, the rotating magnets can instead be made longer than the stationary magnets.

In addition, the shapes of the stationary magnets and rotating magnets and the numbers thereof are not limited to those of the embodiment described in the foregoing.

The invention described above makes it possible to realize a centrifugal type artificial heart pump with high safety and reliability in medical applications.

Specifically, since the blood is passed through the blood flow channel formed between the outer wall of the stator and the inner wall of the casing, a high blood flow rate without high shear stress can be established.

Further, the rotor is not only supported by the suspending action of a large magnetic repulsion force but is also imparted with a force acting to press the pivot onto the floor of the casing. As a result, the rotor can be constantly maintained in the proper attitude during operation more effectively than is possible in prior art artificial heart pumps employing a pivot for mechanical support. Since movement of the rotor in the axial direction is also prevented by the same force, the artificial heart pump does not produce vibration or noise and has a long service life.

Moreover, the artificial heart pump according to the invention exerts less shearing force on the blood it pumps and, as a consequence, causes less hemolysis than do the conventional pumps that have blood flow channels that are formed through a narrow space inside the rotor and sharply deflect the blood flow in the radial direction.

Since the magnetic suspension gap is at a small radial location, the rotational velocity at this portion is small. The risk of thrombogenesis and hemolysis is thus proportionally lower.

The artificial heart pump according to the invention is further designed to prevent blood from stagnating at the rear surface of the impeller and is also better able to prevent blood from stagnating on the outer surface of the rotor than are prior art pumps which pass blood through the center of their rotors. In addition, since blood exiting from the blood flow channel is directed through the washout holes toward the pivot, it is possible to prevent the thrombogenesis that tends to occur in conventional artificial heart pumps owing to stagnation of blood between the center of the rear side of the impeller and the inner surface of the casing.

The patient implanted with the artificial heart pump according to the present invention can therefore be assured that it will provide him or her with stable, long-term service.

What is claimed is:

1. An artificial heart pump comprising:
   a cylindrical casing closed at one end by a floor,
   a rotor rotatably disposed in the casing,
   a cylindrical stator provided between the casing and the rotor and establishing a blood flow channel between its outer surface and the inner surface of the casing,
   an impeller provided to rotate integrally with the rotor for imparting centrifugal force to blood flowing through the blood flow channel,
   stationary magnetic means constituted as at least one permanent magnet provided on the inner surface of the stator,
   rotating magnetic means constituted as at least one permanent magnet provided on the rotor for producing between itself and the stationary magnetic means a force of magnetic repulsion for supporting the rotor in a noncontacting state with respect to the stator, and
   a pivot provided at the rotational center of a rear surface of the impeller to abut on the floor of the casing.

2. An artificial heart pump according to claim 1, wherein the stationary magnetic means and the rotating magnetic means are magnets whose N-S pole directions are aligned parallel with the axis of rotation of the rotor.

3. An artificial heart pump according to claim 2, wherein the magnet constituting the stationary magnetic means and the magnet constituting the rotating magnetic means differ in length and the boundary between the N and S poles of the rotating magnet is positioned closer to the pivot than the boundary between the N and S poles of the stationary magnet.

4. An artificial heart pump according to claim 1, wherein the impeller is provided with at least one washout hole communicating its front and rear surfaces.

5. An artificial heart pump according to claim 1, wherein the stator is fixed at a prescribed spacing from the inner surface of the casing by stays.

* * * * *